(12) United States Patent
Keil et al.

(10) Patent No.: US 6,367,192 B1
(45) Date of Patent: Apr. 9, 2002

(54) FLY PEST CONTROL IN MUSHROOM CULTIVATION

(75) Inventors: Clifford B. O. Keil, Newark, DE (US); Peter Alonzo, Jr., Kennett Square, PA (US); Dennis W. Wheeler, Dayton, NV (US)

(73) Assignees: Sylvan America, Inc., Dayton, NV (US); Pietro Industries, Inc., Kennett Square, PA (US)

( * ) Notice: Subject to any disclaimer, the term of this patent is extended or adjusted under 35 U.S.C. 154(b) by 0 days.

(21) Appl. No.: 09/580,673

(22) Filed: May 30, 2000

Related U.S. Application Data (63) Continuation-in-part of application No. 09/321,318, filed on May 27, 1999.

(51) Int. Cl.⁷ ................................................. A01G 1/04
(52) U.S. Cl. ............................................................. 47/1.1
(58) Field of Search ........................................... 47/1.1

(56) References Cited

U.S. PATENT DOCUMENTS

| | | | |
|---|---|---|---|
| 3,820,278 A | 6/1974 | Giasante | |
| 4,061,488 A | 12/1977 | Mann | |
| 4,384,002 A | 5/1983 | Stoller | |
| 4,617,047 A | * 10/1986 | Bretzloff | 71/5 |
| 4,695,462 A | 9/1987 | Barnes et al. | |
| 4,764,199 A | * 8/1988 | Pratt et al. | 47/1.1 X |
| 4,975,105 A | 12/1990 | Kremer et al. | |
| 4,990,173 A | 2/1991 | Katz et al. | |
| 4,992,275 A | * 2/1991 | Lush | 424/408 |
| 5,106,620 A | 4/1992 | Hickle et al. | |
| 5,106,648 A | 4/1992 | Williams | |
| 5,185,148 A | 2/1993 | Michaels et al. | |
| 5,208,017 A | 5/1993 | Bradfisch et al. | |
| 5,211,946 A | 5/1993 | Payne et al. | |
| 5,262,160 A | 11/1993 | Payne et al. | |
| 5,262,232 A | 11/1993 | Wilfong et al. | |
| 5,266,483 A | 11/1993 | Iizuka et al. | |
| 5,277,906 A | 1/1994 | Zaehner et al. | |
| 5,298,245 A | 3/1994 | Payne et al. | |
| 5,512,279 A | 4/1996 | Jarrett et al. | |
| 5,635,480 A | 6/1997 | Payne et al. | |
| 5,753,222 A | 5/1998 | Marrone et al. | |
| 5,882,670 A | 3/1999 | Wada et al. | |
| 6,156,308 A | * 12/2000 | Liu et al. | 424/93.461 |

FOREIGN PATENT DOCUMENTS

| | | |
|---|---|---|
| WO | WO 96/38044 | 12/1996 |
| WO | WO 87/01910 | 4/1997 |

OTHER PUBLICATIONS

Keil et al., "Interaction of Agaricus bisporus with Bacillus thuringiensis var. israelensis applied for control of *Lycoriella mali*", *Science and Cultivation of Edible Fungi*, Ellio, 1995, p. 532.

Keil, "Field and Laboratory Evaluation of a Bacillus thuringiensis var. israelensis Formulation for Control of Fly Pests of Mushrooms", *Entomological Society of America*, 1991, pp. 1180–1187.

Keil, "*Bacillus thuringiensis israelensis* for Control of Flies in Mushroom Culture", *Mushroom News*, May, pp. 4–10.

(List continued on next page.)

*Primary Examiner*—Charles T. Jordan
*Assistant Examiner*—Jeffrey L. Gellner
(74) *Attorney, Agent, or Firm*—Woodcock Washburn LLP (57) ABSTRACT

The present invention is directed to the field of dipteran pest control in the commercial production of mushrooms. The present invention is directed to preparations comprising mushroom spawn, compost, and casing mixed with thermophilic, spore forming bacteria and supplement, as well as methods for the use of such preparations for the control of Dipteran pests and the production of improved mushroom crops.

76 Claims, 2 Drawing Sheets

Concentration - mortality analysis of two experimental technical powders of *Bacillus thuringiensis* var. *israelensis* compared with Vectobac 12AS against *Lycoriella mali* (Diptera:Sciaridac)

| Formulation | N | Slope±SE | $LC_{50}$ | $LC_{90}$ |
|---|---|---|---|---|
| Vectobac 12AS | 150 | 2.08±0.38 | 478 (302.4-630.0) | 2898 (1915-6350) |
| 22-808BD | 229 | 2.14±0.30 | 568.7 (460.0-715.2) | 2231 (1558-4108) |
| 22-809BD | 222 | 1.99±0.29 | 439.9 (348.1-554.2) | 1926 (1317-3649) |

Potency of the formulations were as follows: Vectobac 12AS 1200 ITU/mg, 22-808BD 6132 ITU/mg, 22-809BD 12160 ITU/mg. LC values are expressed as ITU/larva, about 10 larvae/plate, 3 replications for each dose.
Slopes and LC values for each formulation were not significantly different.
*L. mali* larvae were assayed at fourth instar on water agar plates treated with appropriate concentrations of BTI formulations. Mortality was assessed at 48 hours after exposure of larvae.

OTHER PUBLICATIONS

White et al., "The Story of a strain: Development of GC327, a diptern–active strain of *Bacillus thuringiensis* effective against the mushroom sciarid, Lyucorieel auripila", *Sciene and Cultivation of Edible Fungi*, 1995, pp. 499–506.

Wyatt et al., "The efficient of spawning machines for mixing insecticides into mushroom compost" *Amm. Appl. Biol*, 1974, 78, 125–138.

Cantwell et al., "Effectiveness of Bacillus thurgiensis var. israelensis in Controlling a Sciarid Fly, *Lycoriella mali*, in Mushroom Compost" *J. Econ. Entomol.*, 1984, 77, pp. 473–475.

White. "Comparative effects of three insect growth regulator insecticides and a dipteran–active strain of *Bacillus thuringiensis* on cropping of the cultivated mushroom" *Annals of Applied Biology*, 1999, 134(1) pp. 35–43 (1200245.

Bulla, Jr., et al. "Purification and Characterization of the Entomocidal Protoxin of *Bacillus thuringiensis", The Journal of Biological Chemistry*, vol. 256 No. 6 Mar. 25, 1981, pp. 3000–3004.

Cantwell et al. "The Potential Use of the microbial insecticide Bacillus Thuringiensis var. israelensis to control sciarid larvae", *Mushroom News*, May 1982, pp. 20–21.

Carroll Jr., "Delayed Release Nutrient Supplement for Mushroom Culture", *Applied and Environmental Microbiology*, Apr. 1976, pp. 499–503.

Goldbergh et al. "A Bacterial spore demonstrating rapid larvicidal activity against anopheles sergentii, uranotaenia unguiculata, culex univitattusm aedes aegypti and culex pipiens", *Mosquito News*, Sep. 1977, pp. 355–358.

White, P.F., "Comparative effects of three insect growth regulator insecticides and a dipteran–active strain of *Bacillus thuringiensis* on cropping of the cultivated mushroom *Agaricus bisporus," Ann. Appl. Biol.*, 1999, 134, 35–43.

* cited by examiner

FIG. 1

Concentration - mortality analysis of two experimental technical powders of *Bacillus thuringiensis* var. *israelensis* compared with Vect

FIG. 2

FLY PEST CONTROL IN MUSHROOM CULTIVATION

RELATED APPLICATIONS

This application is a continuation in part application of U.S. Ser. No. 09/321,318 filed May 27, 1999, the disclosures of which are herein incorporated by reference.

FIELD OF THE INVENTION

The present invention relates to the field of fly pest control in the production of mushrooms, and more particularly to thermophilic, spore forming bacteria and supplements for the control of dipteran pests in the production of high quality mushroom crops.

BACKGROUND OF THE INVENTION

The commercial production of mushrooms is a major commercial industry throughout many parts of the world. For example, the production of the commercial mushroom *Agaricus bisporus* in the United States was valued at $777 million in 1996–1997. The control of fly pests, Diptera, is an important component of producing high yielding, quality crops of such mushrooms. Unfortunately, the reliable control of such pests has been complicated by the development of resistance to pesticides, toxicity of pesticides to mushroom mycelium, persistent pesticide residues in the compost/casing material and concerns about exposure of workers to toxic pesticides. Consequently, new types of pesticide preparations and methods of application are necessary for the continued production of commercial mushrooms.

*Lycoriella mali* ("*L. mali*") (Diptera:Sciaridae) is a major insect pest in the commercial production of mushrooms in the United States, Canada, Asia and Australia. *L. mali* is capable of reducing mushroom production by 85-90% in the absence of larvicides and adulticides. While the damage caused by first generation larvae is generally inconsequential, the production of mature fruiting bodies may be significantly affected by second generation larvae actively feeding on the developing mushroom primordia. Additional generations of *L. mali* may develop during the six week cyclic harvesting period, further affecting the production of mushrooms. In addition, adult flies can be a significant factor in the spread of a number of mushroom diseases including *Verticillium fungicola, Pseudomonas tolassi* and *Trichoderma harzianum*. The control of adult *L. mali* is thus important to prevent additional oviposition and mechanical transmission of mushroom pathogens.

The infestation of adult *L. mali* flies generally occurs as the compost cools and during the introduction of spawn into the compost. Female flies oviposit in the compost and the developing larvae feed actively on the compost and the developing mycelium of the mushroom crop. When the casing layer is applied, the larvae may move into this layer to continue feeding on the developing mycelium. As mushroom fruiting bodies begin to develop, the first generation of flies derived from the oviposition begin to emerge. These first generation flies mate and lay additional eggs in the compost and casing layers. Larvae from these eggs will feed on the mycelium. In high numbers, this second as well as subsequent generations of larvae will damage mushroom primordia and tunnel into the stipes of maturing mushrooms.

Current methods of controlling *L. mali* and other fly pests include the use of larvicides and adulticides. Commonly used larvicides include diflubenzuron, cyromazine and methoprene while permethrin and dichlorvos are popular for use as adulticides. However, various problems can be associated with the use of larvicides and adulticides. For example, the larvicide methoprene is only effective against first generation larvae, while larvae have developed resistance to diflubenzuron as well as many adulticides in current use. It has been estimated that *L. mali* can reduce mushroom yields by about 20% with the current pesticide applications in use.

Certain studies have experimented with the thermophilic, spore forming bacteria *Bacillus thuringiensis* var. *israelensis* ("BTi") for the control of *L. mali*. For example, it has been demonstrated that a liquid formulation of BTi sold as Vectobac 12AS (Abbott Laboratories, Inc.) can be effective in controlling larval populations of *L mali* when applied to compost and casing in commercial mushroom houses. However, these applications require large amounts of water to insure adequate mixing of the BTi formulation in both the compost and casing. These aqueous applications prove difficult to incorporate into growing strategies. In addition, the cost of Vectobac, developed primarily for applications in water for control of public health pests, is high. Liquid BTi, thus, is not viewed as acceptable by commercial mushroom producers. There is a need of the development of new methods of controlling fly pests and the production of quality crops in high yields.

SUMMARY OF THE INVENTION

The present invention generally relates to the control of fly pests for improved mushroom production. The present invention relates to preparations comprising mushroom spawn, mushroom compost and thermophilic, spore forming bacteria. The present invention also relates to preparations comprising thermophilic, spore forming bacteria and mushroom casing materials. The invention also relates to preparations comprising supplement combined with thermophilic, spore forming bacteria. Additionally, the invention provides methods of using the preparations of the present invention for the control of fly pests and the improved production of mushroom crops.

The present invention is based in part on the discovery that certain thermophilic, spore forming bacteria preparations may effectively control fly pests during the production of mushrooms. The present invention is further based on the discovery that preparations of supplement combined with certain thermophilic, spore forming bacteria may effectively control fly pests during the production of mushrooms. Such improved preparations and methods for their use are highly useful for the continuation of quality mushroom crops in high yields.

For purposes of the present invention the term "compost" may be used interchangeably with the phrase "growth medium".

The term "free water" refers to that water not normally contained in compost or casing. For example, compost typically contains from about 65 to 75% water (i.e., dry weight-average moisture content of 65–75%). Any additional water added to the compost can be referred to as "free water". For purposes of the present invention, the term "dry" may be used to refer to those compositions, formulations and other preparations characterized by a substantial absence of "free water".

By the phrase "substantial free water", Applicants intend to distinguish over prior practices of applying aqueous solutions or dispersions to mushroom beds and materials. Absolute dryness is not required, however, and those skilled in the art will understand this practical distinction from the context of this invention.

In commercial mushroom culture, a bed of growth medium is generally prepared from any or a combination of organic materials such as prepared straw, horse manure, bagasse, crop residue, animal bedding, chicken feathers and any of a host of other substances such as hay, gypsum, sawdust, straw, soybean products, urea and the like. The growth medium is then inoculated with mushroom spawn. Mushroom spawn is generally comprised of an organic carrier, such as partially cooked grain, optional and well-known adjuvants, and mushroom mycelium. The mycelium is conventionally grown in situ and derives from an inoculum produced from the species or variety of mushroom to be grown. The inoculated grain or other substrate is then allowed to incubate under conditions of time, temperature and humidity applicable to the particular species being grown. The inoculum invades the substrate with networks of mycelium to form the spawn.

The growth medium is typically loaded into suitable growing containers, movable trays, stationary beds or other containers. These containers are typically from 6 to 12 inches deep and contain about 7 to 14 pounds of growth medium per square foot (dry eight-average moisture content of 65–75%). The growth medium is allowed to ferment in the containers to produce a pasteurized selective medium for the growth of mushrooms including Agaricus mushrooms. Although heat is produced during the fermentation process via microbial metabolism, this heat can be supplemented with steam or electric heat to pasteurize the growth medium at about 140° F. The growth medium is then allowed to cool slowly over about 5 days to about 70° F. to 75° F. before inoculation with spawn (e.g., mushroom mycelium grown on sterile rye, wheat or millet grains).

The spawn, that is, the substrate with attendant mycelium, is then applied to the growth medium. The spawn is generally mixed into the growth medium at about 2 to 2.5% be weight in order to start the mycelial growth phase of the crop (i.e., spawn run). Many mushroom growers in the United States and Europe also add supplements including soy, corn or further meal preparations to the compost as a source of protein and lipids for nutrition value to the mushroom crop and to maximize yield. These supplements are often stabilized by denaturation of the proteins and/or coated with or without certain antimicrobial agents, for delayed release and to slow the growth of any potential contaminating fungi. Supplements are generally added to the compost at a concentration of 0.225 to 0.3 lb./ft$^2$(3–4.5%).

The mushroom mycelium invades the growth medium, deriving nutrition therefrom. The resulting mycelial network provides the basis for subsequent fruiting of mushrooms from the mushroom bed. In accordance with certain preferred embodiments of mycoculture, a casing material is applied to the compost some time after application of the spawn. Casing material, which is known per se, is further organic material, and may include peat moss or other soils mixed with hydrated lime and crushed limestone. It is believed that the casing layer spurs the rapid and profound development of mushroom fruiting bodies from the bed while providing water for the developing mushrooms.

Mushroom fruiting bodies appear after the casing is colonized by the mycelium provided the grower provides correct and conventionally known environmental stimuli such as lowered air temperatures and reduced carbon dioxide concentrations. Harvesting of mature mushroom fruit generally occurs in cycles over approximately a six-week period. This can result in several so-called "breaks" of mushrooms being harvested from the beds. For example, after an initial development or break of mushrooms from a bed and their harvest, a further period of time will typically find the emergence of one or more further breaks for harvest. In some practices, additional nutrients are applied to the bed to provoke or nourish such further development. All of the foregoing are well known to persons of ordinary skill in the art and science of mycoculture.

Unfortunately, dipteran pests such as the fly *L. mali* are known to invade mushroom production facilities during the cooling of growth medium as well as during the mixing of the spawn with growth medium. Female flies may oviposit in the growth medium and the resulting generations of larvae may feed actively on the growth medium and the developing mycelium of the mushroom crop. Larvae may also move into the casing layer to feed on mycelium as it colonizes the casing. In high numbers, larvae may damage mushroom primordia and tunnel into the stipes of maturing mushrooms.

It is clear that the control of flies is an extremely important factor in growing high quality crops with optimal yields. Many studies have focused on the addition of pesticides to growth medium and casing. Some studies have focused on the addition of thermophilic, spore forming bacteria to growth medium and casing. When certain thermophilic, spore forming bacteria are grown to lysis under appropriate conditions, the bacteria produce spores and protein crystals containing two or more insecticidal proteins highly useful in mycoculture. The spore may be considered the dormant form of the bacteria as is known to those skilled in the art. When ingested by susceptible insect larvae, the crystal protein dissolves and attacks the insect's gut. Eventually, the toxin proteins result in the death of the insect. As the developing *L. mali* larvae feed on the growth medium and developing mycelium, they ingest insecticidal protein crystals where thermophilic, spore forming bacteria preparations have been applied to the growth medium or casing. While some studies have focused on the addition of BTi to growth medium and casing, all of these studies have required the addition of free water for effective control of fly pests. For example, Keil has experimented with liquid formulations of BTi for control of both *L. mali* and the phorid, *Megaselia halterata*. Keil et al., Interaction of *Agaricus bisporus* with *Bacillus thuringiensis* var. *israelensis* applied for control of *Lycoriella mali*, in Science and Cultivation of Edible Fungi 525–532 (T. J. Elliot ed. 1995); Keil, Field and laboratory evaluation of a *Bacillus thuringiensis* var. israelensis formulation for control of fly pests of mushrooms, J. Econ. Entomol. 84:1180–1188 (1991); Keil, *Bacillus thuringiensis* var. *israelensis* for control of flies in mushroom culture, Mushroom News 36(5):4–11 (1988).

In U.S. Patent Number 5,512,279, Jarrett et al. discloses results indicating that liquid formulations of the HD541 and HD571 strains of *Bacillus thuringiensis* var. *kyushuensis* can be used for the biological control of Dipteran pests of the genus Lycoriella.

White et al. has studied the development of the GC327 strain of *Bacillus thuringiensis* var. *israelensis* in substantial amounts of water for the control of the mushroom sciarid *Lycoriella auripila*. White et al., The story of a strain: Development of GC327, a dipteran-active strain of *Bacillus thuringiensis* effective against the mushroom sciarid, *Lycoriella auripila*, in Science and Cultivation of Edible Fungi 499–506 (T. J. Elliot ed. 1995).

Wyatt et al. has studied insecticide formulated as emulsifiable concentrates that must, by necessity, be diluted with water before application. Wyatt et al., The efficiency of spawning machines for mixing insecticides into mushroom compost, Annl. Appl. Biol. 78:125–128 (1974).

Cantwell et al. studied the toxicity of an experimental preparation of BTi to *L. mali*, reporting that mortality exceeded 99.5% with a 1:60 dilution. Cantwell et al., Effectiveness of *Bacillus thuringiensis* var. *israelensis* in controlling a sciarid fly, *Lycoriella mali*, in mushroom compost, J. Econ. Entomol. 77:473–475 (1984). Cantwell et al. also reported that two commercial preparations containing Bti tested at a dilution of 1:100 produced mortality rates of either 79.2% or 94.4%. See id.

The presence of free water can adversely inhibit mushroom yield in several ways. First, the proliferation of the spawn can be retarded if the free water level in the compost is too high. Second, the presence of too much free water in the compost can make the mushroom crop more susceptible to *Trichoderma harzianum*. Third, the potential for "mummy disease" may be increased by the application of water to the compost soon after spawning. Finally, the addition of water can magnify the natural heterogeneity of the compost by providing straight paths for water to run through. There is thus a need for preparations and methods that can effectively control fly pests without harming mushroom crops or yields.

It is thus to be understood that certain embodiments of the present invention are based on the discovery that certain thermophilic, spore forming bacteria may form preparations characterized by an absence of substantial free water for the effective control of fly pests. For purposes of the present invention, it is to be understood that the phrase "thermophilic, spore forming bacteria" may include spores and protein crystals containing at least one insecticidal protein, as described above. The phrase "thermophilic, spore forming bacteria" may include spores. The phrase "thermophilic, spore forming bacteria" may include protein crystals containing at least one insecticidal protein. In accordance with certain embodiments of the present invention, the "thermophilic, spore forming bacteria" may be in the form of a powder or suspension.

In accordance with certain embodiments of the present invention, it is preferred that the thermophilic, spore forming bacteria is mixed with mushroom spawn without the addition of substantial free water. The mixed thermophilic, spore forming bacteria and mushroom spawn may be mixed with growth medium. It is preferred that the thermophilic, spore forming bacteria is mixed with growth medium without the addition of substantial free water. The mixed thermophilic, spore forming bacteria and growth medium may be mixed with mushroom spawn. It is also preferred that the thermophilic, spore forming bacteria is mixed with the casing layer without the addition of substantial free water. In all cases, supplement may be combined with the thermophilic, spore forming bacteria, as described below.

In certain embodiments of the present invention, the growth medium is pasteurized by heating. It is preferred that the growth medium is heated at a temperature of about from 120° F. to about 160° F., preferably about 140° F. It is also preferred that the growth medium is heated for a period of about 8 to about 48 hours, preferably from about 10 to about 30 hours. More preferred is that the growth medium is heated about 24 hours. The pasteurized growth medium is allowed to cool to about 70° F. to about 75° F. over a period of about 5 days. The pasteurized and cooled growth medium may then be inoculated with thermophilic, spore forming bacteria without the addition of substantial free water. Mushroom spawn is then mixed into the inoculated growth medium at about 1.5% to about 2.5% by dry weight, without the addition of free water, in order to start the mycelial growth phase or spawn run.

In another embodiment of the present invention, casing is inoculated with thermophilic, spore forming bacteria without the addition of substantial free water. It is preferred that thermophilic, spore forming bacteria is provided on an inert carrier such as vermiculite, peat moss or granulated clay particles. Preferably the inert carrier is vermiculite. More preferred is that the inert carrier is combined or coated with the thermophilic, spore forming bacteria via the coating techniques described below. The inoculated casing layer may be applied to the top surface of the growth medium once the mushroom mycelium has grown above the top surface of the growth medium. It is preferred that the casing layer is from about 1 to about 2 inches thick, preferably 1.5 inches thick.

A variety of thermophilic, spore forming bacteria are suitable for use in the present invention. Those skilled in the art are familiar with a number of known thermophilic, spore forming bacteria effective in the control of a number of species of fly pests. For example, thermophilic, spore forming bacteria suitable for use in the present invention include, by way of example only and without limitation, the bacteria *Bacillus thuringiensis israelensis, Bacillus thuringiensis dendrolimus, Bacillus thuringiensis kyushuensis* and *Bacillus thuringiensis morrisoni*. Preferably the thermophilic, spore forming bacteria is *Bacillus thuringiensis israelensis* (BTi) and/or *Bacillus thuringiensis kyushuensis* (BTk). More preferred is that the thermophilic, spore forming bacteria is *Bacillus thuringiensis israelensis.*

The potency of thermophilic, spore forming preparations can be measured by bioassay against *Aedes aegypti* mosquitoes and is expressed in International Toxic Units (ITU). For example, the liquid BTi formulation Vectobac 12AS (Abbott Laboratories, Inc.) has a potency of 1.26 billion ITU per liter or 1,200 ITU per mg. Another liquid BTi formulation, sold as Gnatrol (Abbott Laboratories), has a potency of 600 million ITU per liter. A technical powder BTi formulation, also available from Abbott Laboratories, has a potency of about 5,000 ITU per mg. In addition, two experimental technical powders of BTi have been developed having the designations 22-808BD ("808") and 22-809BD ("809") and respective potencies of 6,132 ITU per mg and 12,160 ITU per mg. Concentration-mortality analyses for 22-808BD and 22-809BD are provided at FIGS. 1 and 2.

It is well-known to those skilled in the art that application rates of the thermophilic, spore forming bacteria can vary with the particular variety of bacteria. By way of example, and without limitation, BTi powder formulations can range from about 0.60 to about 4.25 g/$ft^2$ of compost surface. It is preferred that the effective application rate is from about 6 to about 21 million ITU/$ft^2$ for potencies ranging from about 5,000 to about 12,160 ITU/mg. It is presently believed that application rates below about 6 million ITU/$ft^2$ are not sufficiently effective in controlling fly pests while application rates above about 21 million ITU/$ft^2$ are not satisfactory from a cost/benefit standpoint. Again by way of example, and without limitation, BTi powder formulations can range from about 0.5 to about 3 g/ft² of casing surface. It is preferred that the effective application rate is from about 2 to about 6 million ITU/ft² for potencies ranging from about 5,000 to about 12,160 ITU/mg. It is presently believed that application rates below about 2 million ITU/ft² are not effective in controlling fly pests while rates above about 6 million ITU/ft² are not satisfactory from a cost/benefit standpoint and may reduce mushroom yields.

In accordance with certain embodiments of the present invention, supplements may be added to the growth medium and/or casing. Supplement may be provided as a source of protein and lipid for nutrition value and are generally added to compost at the time of inoculation with spawn. Supplements are well known to those skilled in the art and may include, by way of example, soy, corn, feather or other similar meal preparations. It is preferred that the supplements are added at a concentration of from about 0.1 to about 0.3 lbs. per square foot or from about 1.0 to about 6.0% by dry weight. In general, from about 100 to about 450 pounds of product per 1000 ft² of growing surface is appropriate when using preferred BTi-supplement combinations.

It is further to be understood that certain embodiments of the present invention are based on the discovery that supplement combined with thermophilic, spore forming bacteria can effectively control fly pests. A practice well-known to those skilled in the art of mycoculture is to add supplements during spawning or casing in order to provide nutrition for the developing mycelia. These supplements are generally treated to protect them against other microorganisms present in the compost that would otherwise use the supplement as a food source. The mushroom fungus, however, with its more specialized physiology, can offset this special treatment and use the nutrients of the supplement.

One common method for the treatment of supplements is to chemically denature protein supplements with compounds such as formaldehyde. In addition, individual supplement particles can be physically coated or enrobed with a protective barrier. However, the coating of supplements provides for unique benefits in the art and science of mycoculture. For example, coated supplements can act as an excellent vehicle for conveying important compounds into mushroom compost and casing. In addition to nutritional compounds, non- nutritional compounds can be incorporated into the coating of each individual supplement particle. In particular, pesticides including thermophilic, spore forming bacteria can be incorporated into the coating of a mushroom supplement particle for effective fly pest control in the production of mushrooms. It is preferred that supplements are coated with a hydrophilic compound containing a microbe-inhibiting agent as described in U.S. Pat. No. 4,990,173, the disclosures of which are hereby incorporated by reference in their entirety. It is also preferred that the supplements are prepared according to U.S. Pat. No. 4,764,199 and U.S. Ser. No. 09/506,759, the disclosures of which are hereby incorporated by reference in their entirety.

A variety of coating techniques known to those skilled in the art are suitable for the combining of supplement and thermophilic, spore forming bacteria in accordance with the present invention. Such suitable coating techniques may include, by way of example, pan ("drum") coating, fluid-bed coating, air-suspension coating and spray-dry coating. Thermophilic, spore forming bacteria may be added to a liquid carrier or solvent. A solution (liquid to viscous slurry) may prepared into which a thermophilic, spore forming bacteria slurry, technical powder or water-soluble formulation is added. While a wide variety of liquids can be used to prepare a coating dispersion or solution, water is preferred for convenience and economy.

The resulting coating formulation can be conveyed to the supplement substrate using, for example, peristaltic pumps. The coating formulation is sprayed and atomized onto the substrate in the desired concentration. The substrate is preferably agitated in order to ensure the even coating of all regular and irregular particle surfaces. Drying is begun immediately upon contact of the formulation with the substrate. It is preferred that the drying temperature is maintained below about 60° C. in order to prevent destruction of the thermophilic, spore forming bacteria. Assays may be utilized in order to determine the proper uptake of thermophilic, spore forming bacteria by the substrate.

Tests comparing the efficacy of various thermophilic, spore forming bacteria powder formulations against current pesticide applications have been conducted in commercial mushroom facilities. These field tests can be summarized in the examples as described below.

EXAMPLES

Example 1

Three mushroom beds denoted Example 1, Control A and Control B were prepared by initially mixing growth medium having a growing surface area of about 7,400 ft² with Agaricus spawn. The growth medium of Example 1 was also mixed with a preparation of 25.67 pounds of BTi powder having a potency of 5,000 ITU/mg mixed with 1,750 pounds of mushroom supplement. BTi was thus provided at an effective application rate of about 7.9 million ITU/ft². A casing layer was applied to the top surface of each growth medium after about 16 days (i.e., a spawn run of about 16 days). The casing layers of both Control A and Control B were treated with Dimilin (Uniroyal), a diflubenzuron formulation currently used for fly pest control, applied at label rates.

Example 1 was physically located between Control A and Control B. Emergence traps and black light traps were used to measure the number of adult flies captured per minute. Emergence trap counts are the average total flies per trap. Black light trap counts are expressed as total flies captured per minute.

TABLE 1

| | *L. mali* Adult Flies Captured | | |
|---|---|---|---|
| | Control A (Dimilin treated casing) | Example 1 (BTi treated growth medium) | Control B (Dimilin treated casing) |
| Emergence Traps (flies/minute) | | | |
| Mean L. mali | 16.83 ± 3.98 | 8.83 ± 3.03 | 20.33 ± 5.26 |
| Black Light Traps (flies/minute) | | | |
| Before 2nd Break | 5.7 ± 1.2 | 4.7 ± 0.7 | 7.7 ± 2.6 |
| After 2nd Break | 10.7 ± 1.8 | 7.3 ± 0.7 | 18.3 ± 2.0 |
| Before 3rd Break | 22.0 ± 3.6 | 10.3 ± 1.5 | 17.3 ± 1.5 |
| After 3rd Break | 27.3 ± 3.3 | 13.7 ± 1.5 | 37.0 ± 3.2 |

Referring to Table 1, Example 1 resulted in a lower adult fly count as compared to Control A and Control B. The results are reported as means with associated standard errors. All results are statistically significant except for the measurement taken before the 2nd break. Improved fly control and mushroom yield can be provided where BTi is mixed with growth medium at a rate of about 5 million ITU/ft$^2$.

Example 2

Two mushroom beds denoted Example 1 and Control A were prepared by initially mixing growth medium with Agaricus spawn. The growth medium of Example 1 was also mixed with a preparation of BTi powder having a potency of 5,000 ITU/mg mixed with supplement. BTi was thus provided at a rate of about 6.8 million ITU/ft$^2$. A casing layer was then applied to the top surface of each growth medium. The casing layer of Control A was treated with Dimilin applied at a rate of about 0.45 g/ft$^2$. Emergence traps estimated the emergence of L. mali before the first harvest.

TABLE 2

|  | L. mali Adult Flies Captured | |
| --- | --- | --- |
|  | Example 1 (BTi treated growth medium) | Control A (Dimilin treated casing) |
| Emergence Traps (flies/minute) | | |
| Mean L.mali | 2.3 ± 0.6 | 7.3 ± 0.9 |

Figure 1:
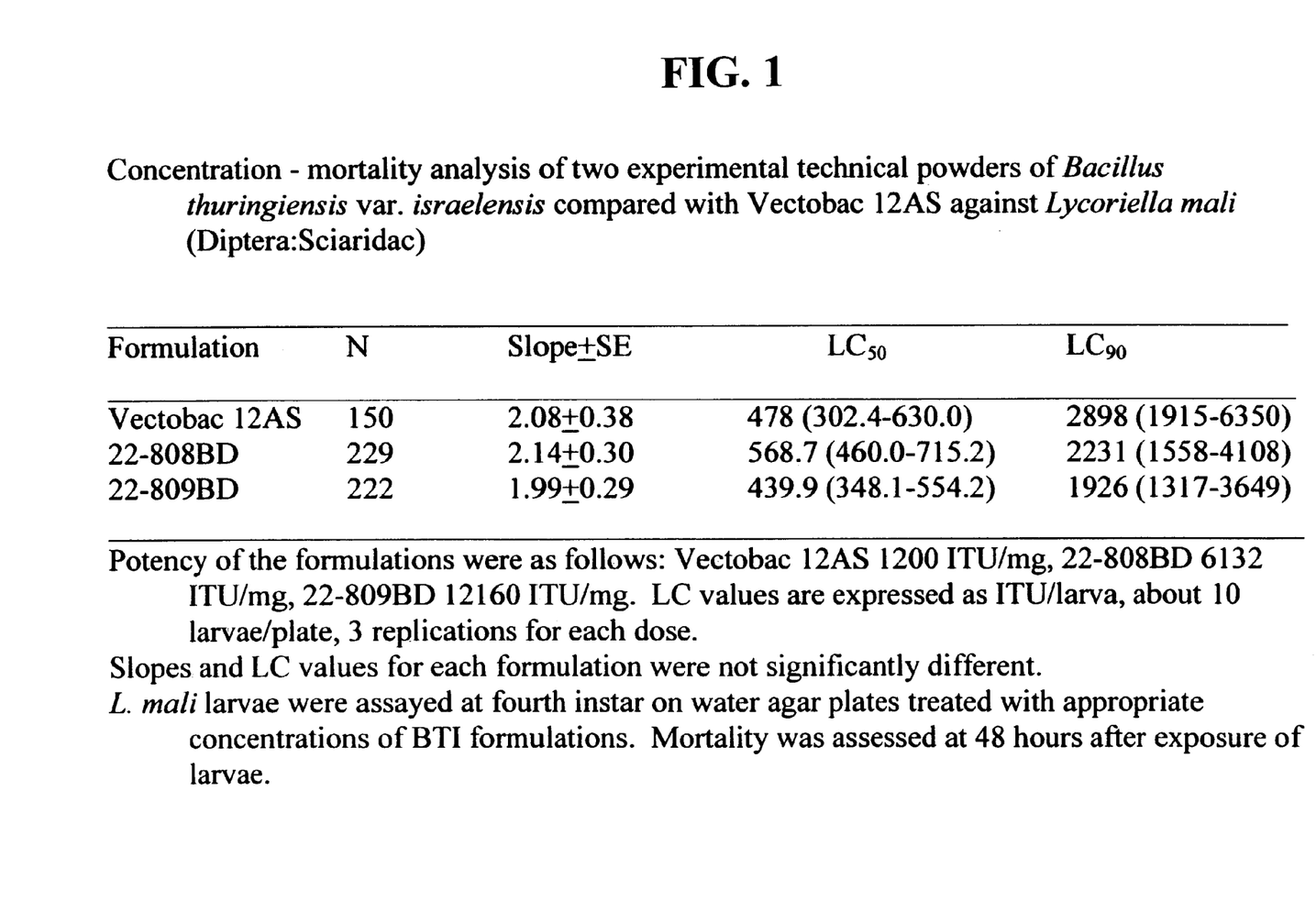
FIG. 1 depicts a concentration-mortality analysis of BTi powders relative to Vectobac 12AS against *L. mali* in accordance with certain preferred embodiments of the present invention.
Figure 2:
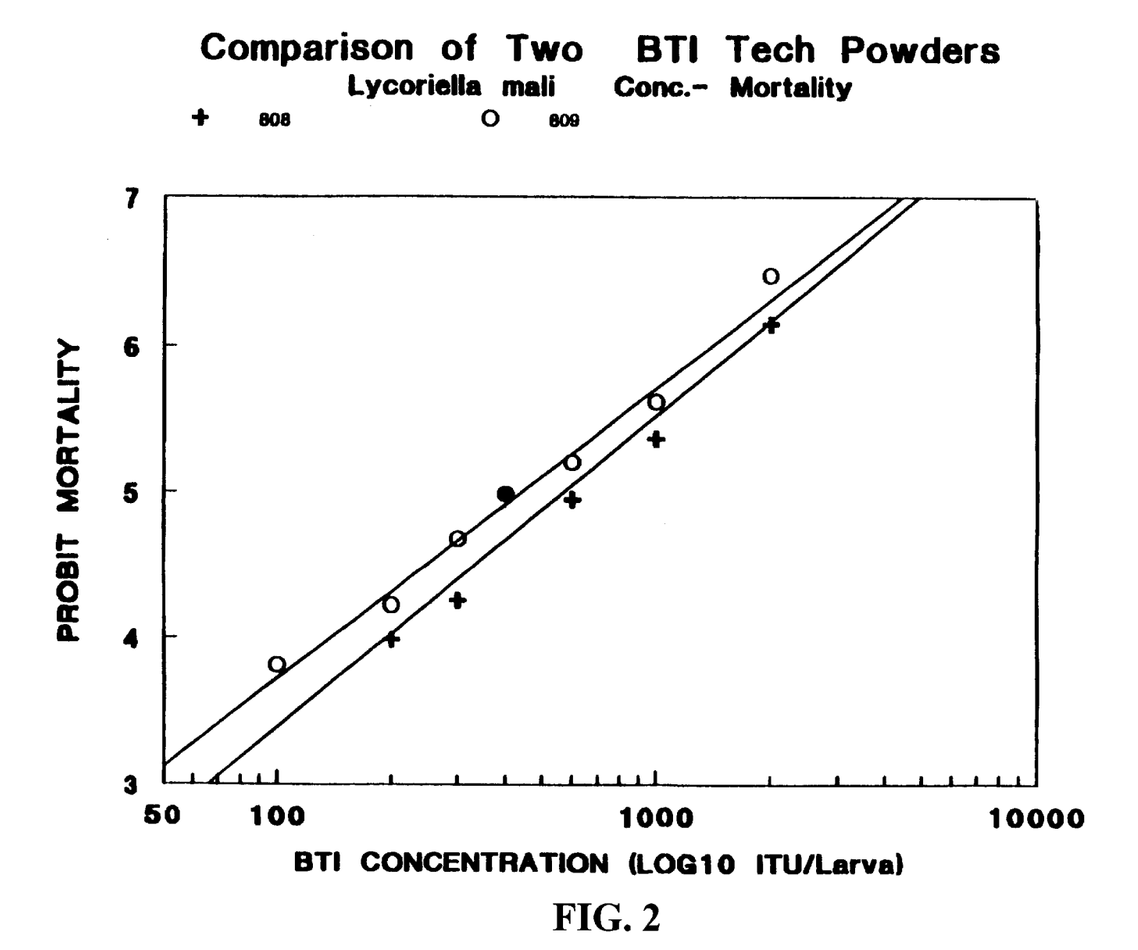
FIG. 2 is a graphic illustration illustrating a concentration-mortality analysis of BTi powders in accordance with certain preferred embodiments of the present invention.

With reference to FIG. 2, Example 1 produced a lower adult fly count as compared to Control A. The difference was statistically significant. Improved fly control and mushroom yield can be provided where BTi is mixed with growth medium at a rate of about 6.8 million ITU/ft$^2$.

Example 3

The general procedure of EXAMPLE 1 was followed in order to prepare four mushroom beds denoted Example 1, Example 2, Control A and Control B. However, the growth medium of both Example 1 and Example 2 were mixed with a corn gluten supplement comprising 60% protein (commercially available as CG-60) coated with a BTi toxin crystal-spore suspension such as the Vectobac 12 AS liquid. The growth medium of both Control A and Control B was mixed with corn gluten supplement.

Twelve 50 gram samples were removed from each mushroom bed. Each sample was placed in a test cup along with ten 2nd instar L. mali. The samples were misted to maintain moisture levels. Each test cup was covered with semipermeable plastic film to allow gas exchange. Adult flies were counted on emergence.

TABLE 3

| Example | Treated Bed | Sample Size (N) | Mean Emergence of Adult L. mali |
| --- | --- | --- | --- |
| Control A | 12 | 12 | 7.92 ± 0.48 |
| Control B | 42 | 12 | 8.50 ± 0.38 |
|  | Total | 24 | 8.21 ± 0.31 |
| Example 1 | 22 | 12 | 0.67 ± 0.22 |
| Example 2 | 32 | 12 | 0.92 ± 0.26 |
|  | Total | 24 | 0.79 ± 0.17 |

Referring to Table 3, the fly count for both Example 1 and Example 2 was significantly lower than for Control A and Control B. All differences were statistically significant.

Example 4

The general procedure of EXAMPLE 3 was followed in order to prepare four mushroom beds denoted Example 1, Example 2, Control A and Control B. The growth medium of both Example 1 and Example 2 was mixed with corn gluten supplement coated with a BTi toxin crystal-spore suspension such as Vectobac 12 AS liquid. The growth medium of both Control A and Control B was mixed with corn gluten supplement.

Twelve 50 gram samples were removed from each mushroom bed and each sample placed in a test cup. However, twenty 2nd instar L. mali were placed in each cup with the samples instead of ten 2nd instar L. mali. The samples were misted to maintain moisture levels. Each test cup was covered with semipermeable plastic film to allow gas exchange. Adult flies were counted on emergence.

TABLE 4

| Example | Treated Bed | N | Mean Emergence of Adult L. mali |
| --- | --- | --- | --- |
| Control A | 32 | 12 | 17.3 ± 0.8 |
| Control B | 42 | 12 | 17.1 ± 0.7 |
|  | Total | 24 | 17.2 ± 0.5 |
| Example 1 | 22 | 12 | 0.8 ± 0.3 |
| Example 2 | 12 | 12 | 1.0 ± 0.3 |
|  | Total | 24 | 0.9 ± 0.2 |

Referring to FIG. 4, the mean emergence from both Examples 1 and 2 (growth medium treated with BTi coated supplement) was, in all cases, significantly lower than the mean emergence from Controls A and B (growth medium treated with supplement).

Example 5

The general procedure of EXAMPLE 4 was repeated to prepare mushroom beds denoted Examples 1–3 and Controls A–C. Example 1 and Control A were contained in a first mushroom house, Example 2 and Control B in a second mushroom house, and Example 3 and Control C in a third mushroom house. The growth medium of Examples 1, 2 and 3 was mixed with corn gluten supplement coated with a BTi toxin crystal-spore suspension such as the Vectobac 12 AS liquid. The growth medium of Controls A, B and C was mixed with corn gluten supplement.

Twelve 50 gram samples were removed from each mushroom bed. Each sample was placed in a test cup along with twenty 2nd instar L. mali. The samples were misted to maintain moisture levels. Each test cup was covered with semipermeable plastic film to allow gas exchange. Adult flies were counted on emergence.

TABLE 5

|  | N | Mean Emergence ± S.E. |
| --- | --- | --- |
| Example 1 | 3 | 7.7 ± 1.3 |
| Control A | 3 | 18.3 ± 3.2 |
| Example 2 | 4 | 1.3 ± 0.6 |
| Control B | 4 | 5.8 ± 0.6 |
| Example 3 | 4 | 7.8 ± 1.8 |
| Control C | 4 | 13.0 ± 3.4 |

With reference to Table 5, while the level of natural fly infestation was significantly different in the three mushroom houses, the emergence of flies from Examples 1–3 (BTi coated supplement) was, in all cases, significantly lower than the emergence of flies from Controls A–C (supplement). The results of Table 5 indicate that the suppression of fly emergence from Examples 1–3 is acceptable for commercial mushroom production.

Example 6

The general procedure of EXAMPLE 3 was repeated in order to prepare Examples 1–4 and Control A. However, modifications were made. For example, in all cases the supplements were evaluated on water agar plates instead of growth medium in determining fly mortality. In addition, while Example 1 included the corn gluten supplement coated with a BTi toxin crystal-spore suspension, Examples 2–4 included a combination corn-soy meal supplement containing 55% protein. Control A included corn gluten supplement.

TABLE 6

|  | Amount/Plate (g) | N | Mortality ± S.E. (%) |
|---|---|---|---|
| Control A | 0.10 | 4 | 0 |
| Example 1 | 0.10 | 4 | 70.5 ± 6.9 |
| Example 2 | 0.02 | 4 | 62.5 ± 4.8 |
| Example 3 | 0.06 | 4 | 83.9 ± 7.7 |
| Example 4 | 0.10 | 4 | 93.0 ± 4.4 |

With reference to Table 6, the mortality of flies was significantly greater for Examples 1–4 relative to control A.

Example 7

The general procedure of EXAMPLE 5 was followed to produce mushroom beds denoted Example 1, Control A and Control B. The growth medium of Example 1 was mixed with corn gluten supplement coated with Vectobac 12 AS. The growth medium of Control A was mixed with the Vectobac 12 AS. In all cases, Vectobac 12 AS was applied at label rate in 12 gallons of water per bed. The growth medium of Control B was mixed with the corn gluten supplement added dry.

Samples of growth medium were taken from each mushroom bed at 1, 3, 5, 10, and 14 days after spawning, and extracted for ergosterol, a common steroid in fungi. There were no differences in ergosterol content in the samples from Example 1 and Control B (supplement alone). However, the ergosterol content was lower for samples of Control A (Vectobac with water) relative to samples of Example 1 on all but the first and last sampling intervals. In particular, relative to Example 1, the ergosterol content for Control A was 35% lower on day 3, 32% lower on day 5, 23% lower on day 10, and 7% lower on day 14. This confirms that the use of water in conjunction with the thermophilic, spore forming bacteria is detrimental, in that it retards growth of mycelium and increases the potential growth of disease in the crop.

Example 8

Results similar to Table 5 can be obtained where the general procedures of EXAMPLE 5 are repeated with *Megaselia halteratea* (Diptera:Phoridae) instead of *L. mali*.

Each of the patents, patent applications and publications described herein are hereby incorporated by reference in their entirety.

Various modifications of the invention, in addition to those described herein, will be apparent to one skilled in the art in view of the foregoing description. Such modifications are also intended to fall within the scope of the appended claims.

It is to be understood that the specification of the present application hereby incorporates by reference the appended claims and their disclosures in their entirety.

What is claimed is:

1. A mushroom preparation comprising a mixture of:
   (a) mushroom spawn; and,
   (b) thermophilic, spore forming bacteria applied to the spawn, said application having been made without substantial free water.
2. The preparation of claim 1, further comprising mushroom compost.
3. The preparation of claim 1 further comprising mushroom supplement.
4. The preparation of claim 3 wherein the supplement is combined with thermophilic, spore forming bacteria.
5. The preparation of claim 4 wherein the supplement is coated with thermophilic, spore forming bacteria.
6. The preparation of claim 2 wherein the compost has been heated between about 120° and about 160° F. for a period between about 8 and about 48 hours.
7. The preparation of claim 6 wherein the compost has been heated between about 70° and about 75° F.
8. The preparation of claim 2, further comprising supplement.
9. The preparation of claim 8 wherein the supplement is combined with thermophilic, spore forming bacteria.
10. The preparation of claim 9 wherein the supplement is coated with thermophilic, spore forming bacteria.
11. The preparation of claim 1 wherein the thermophilic, spore forming bacteria comprises spores or protein crystals.
12. The preparation of claim 1 wherein the thermophilic, spore forming bacteria is *Bacillus thuringiensis israelensis, Bacillus thuringiensis dendrolimus, Bacillus thuringiensis kyushuensis* or *Bacillus thuringiensis morrisoni*.
13. The preparation of claim 12 wherein the thermophilic, spore forming bacteria is *Bacillus thuringiensis israelensis* or *Bacillus thuringiensis kyushuensis*.
14. The preparation of claim 13 wherein the thermophilic, spore forming bacteria is *Bacillus thuringiensis israelensis*.
15. The preparation of claim 1 wherein the thermophilic, spore forming bacteria has an effective application rate between about 6 and about 21 million ITU/ft$^2$.
16. The preparation of claim 15 wherein the thermophilic, spore forming bacteria has an effective application rate between about 8 and about 19 million ITU/ft$^2$.
17. The preparation of claim 16 wherein the thermophilic, spore forming bacteria has an effective application rate of between about 10 and about 17 million ITU/ft$^2$.
18. The preparation of claim 17 wherein the thermophilic, spore forming bacteria has an effective application rate of between about 12 and about 15 million ITU/ft$^2$.
19. The preparation of claim 15 wherein the thermophilic, spore forming bacteria has an effective application rate of about 8 million ITU/ft$^2$.
20. A mushroom preparation comprising a mixture of:
   (a) mushroom casing; and
   (b) thermophilic, spore forming bacteria applied to the casing, said application having been made without substantial free water.
21. The preparation of claim 20 wherein the thermophilic, spore forming bacteria comprises spores or protein crystals.
22. The preparation of claim 20 wherein the thermophilic, spore forming bacteria is *Bacillus thuringiensis israelensis,*

*Bacillus thuringiensis dendrolimus, Bacillus thuringiensis kyushuensis* or *Bacillus thuringiensis morrisoni*.

23. The preparation of claim 22 wherein the thermophilic, spore forming bacteria is *Bacillus thuringiensis israelensis* or *Bacillus thuringiensis kyushuensis*.

24. The preparation of claim 23 wherein the thermophilic, spore forming bacteria is *Bacillus thuringiensis israelensis*.

25. The preparation of claim 20 wherein the thermophilic, spore forming bacteria has an effective application rate between about 2 and about 6 million ITU/ft$^2$.

26. The preparation of claim 25 wherein the thermophilic, spore forming bacteria has an effective application rate of between about 3 and about 5 million ITU/ft$^2$.

27. The preparation of claim 26 wherein the thermophilic, spore forming bacteria has an effective application rate of about 4 million ITU/ft$^2$.

28. The preparation of claim 20 wherein the casing comprises peat moss and at least one material selected from the group comprising hydrated lime and limestone.

29. The preparation of claim 20 wherein the thermophilic, spore forming bacteria is provided on an inert particulate substrate.

30. The preparation of claim 29 wherein the inert particulate substrate is coated with thermophilic, spore forming bacteria.

31. The preparation of claim 30 wherein the inert particulate substrate is vermiculite.

32. The preparation of claim 20, further comprising the preparation of claim 2.

33. A method for controlling fly pests in the production of mushrooms comprising admixing mushroom spawn and thermophilic, spore forming bacteria, in the absence of substantial free water.

34. The method of claim 33, further comprising admixing mushroom compost.

35. The method of claim 33 further comprising heating compost at a temperature between about 120° and about 160° F. for a period between about 8 and about 48 hours.

36. The method of claim 35 further comprising cooling compost to a temperature between about 70° and about 75° F.

37. The method of claim 33, further comprising admixing supplement.

38. The method of claim 37 wherein the supplement is combined with thermophilic, spore forming bacteria.

39. The method of claim 38 wherein the supplement is coated with thermophilic, spore forming bacteria.

40. The preparation of claim 33 wherein the thermophilic, spore forming bacteria comprises spores or protein crystals.

41. The method of claim 33 wherein the thermophilic, spore forming bacteria is *Bacillus thuringiensis israelensis, Bacillus thuringiensis dendrolimus, Bacillus thuringiensis kyushuensis* and *Bacillus thuringiensis morrisoni*.

42. The method of claim 41 wherein the thermophilic, spore forming bacteria is *Bacillus thuringiensis israelensis* and *Bacillus thuringiensis kyushuensis*.

43. The method of claim 42 wherein the thermophilic, spore forming bacteria is *Bacillus thuringiensis israelensis*.

44. The method of claim 33 wherein the thermophilic, spore forming bacteria has an effective application rate between about 6 and about 21 million ITU/ft$^2$.

45. The method of claim 44 wherein the thermophilic, spore forming bacteria has an effective application rate of between about 8 and about 19 million ITU/ft$^2$.

46. The method of claim 45 wherein the thermophilic, spore forming bacteria has an effective application rate of between about 10 and about 17 million ITU/ft$^2$.

47. The method of claim 46 wherein the thermophilic, spore forming bacteria has an effective application rate between about 12 and about 15 million ITU/ft$^2$.

48. The method of claim 33 wherein the thermophilic, spore forming bacteria has an effective application rate of about 8 million ITU/ft$^2$.

49. A method for controlling fly pests in the production of mushrooms comprising admixing casing and thermophilic, spore forming bacteria, in the absence of substantial free water.

50. The preparation of claim 49 wherein the thermophilic, spore forming bacteria comprises spores or protein crystals.

51. The method of claim 49 wherein the thermophilic, spore forming bacteria is *Bacillus thuringiensis israelensis, Bacillus thuringiensis dendrolimus, Bacillus thuringiensis kyushuensis* or *Bacillus thuringiensis morrisoni*.

52. The method of claim 51 wherein the thermophilic, spore forming bacteria is *Bacillus thuringiensis israelensis* or *Bacillus thuringiensis kyushuensis*.

53. The method of claim 52 wherein the thermophilic, spore forming bacteria is *Bacillus thuringiensis israelensis*.

54. The method of claim 49 wherein the thermophilic, spore forming bacteria has an effective application rate of between about 2 and about 6 million ITU/ft$^2$.

55. The method of claim 54 wherein the thermophilic, spore forming bacteria has an effective application rate of between about 3 and about 5 million ITU/ft$^2$.

56. The method of claim 55 wherein the thermophilic, spore forming bacteria has an effective application rate of about 4 million ITU/ft$^2$.

57. The method of claim 49 wherein the casing comprises peat moss and at least one material selected from the group comprising hydrated lime and limestone.

58. The method of claim 49 wherein the thermophilic, spore forming bacteria is provided on an inert particulate substrate.

59. The method of claim 58 wherein the inert particulate substrate is coated with thermophilic, spore forming bacteria.

60. The method of claim 59 wherein the inert particulate substrate is vermiculite.

61. The method of claim 49 further comprising applying the preparation to mushroom compost.

62. A method for controlling fly pests in the production of mushrooms comprising:
   pasteurizing compost at a temperature of about from 120° to 160° F. for a period of about from 8 to 48 hours;
   cooling the compost to a temperature of about from 70° to 75° F.; admixing the compost with mushroom mycelia and an effective amount of a first dose of thermophilic, spore forming bacteria, in the absence of substantial free water, to produce an inoculated mixture;
   cultivating the inoculated mixture to substantially permeate the compost with the mycelia; and
   applying a casing layer to the top surface of the inoculated mixture, the casing layer comprising peat moss and at least one material selected from hydrated lime and limestone.

63. The method of claim 62 wherein the first dose is combined with a supplement before admixing it with the compost.

64. The method of claim 63 wherein the thermophilic spore forming bacteria is applied to a supplement by combining the bacteria with a liquid carrier, coating the supplement with the bacteria in the liquid carrier, and then drying the resulting coated supplement.

65. The method of claim 64 wherein the liquid carrier consists essentially of water.

66. The method of claim 62 wherein the first dose is mixed with the mushroom spawn before admixing it with the compost.

67. The preparation of claim 62 wherein the thermophilic, spore forming bacteria comprises spores or protein crystals.

68. The method of claim 62 wherein the thermophilic, spore forming bacteria is *Bacillus thuringiensis israelensis, Bacillus thuringiensis dendrolimus, Bacillus thuringiensis kyushuensis* or *Bacillus thuringiensis morrisoni.*

69. The method of claim 68 wherein the thermophilic, spore forming bacteria is *Bacillus thuringiensis israelensis* or *Bacillus thuringiensis kyushuensis.*

70. The method of claim 69 wherein the thermophilic, spore forming bacteria consists essentially of *Bacillus thuringiensis israelensis.*

71. The method of claim 62 wherein the casing layer is admixed with an effective amount of a second dose of a thermophilic, spore forming bacteria, in the absence of substantial free water.

72. The method of claim 71 wherein the second dose is applied at an effective rate of about from 2 to 6 million ITU/ft$^2$.

73. The method of claim 72 wherein the second dose is applied at an effective rate of about 4 million ITU/ft$^2$.

74. The method of claim 72 wherein the second dose of thermophilic spore forming bacteria is applied to an inert particulate substrate.

75. The method of claim 62 wherein the first dose is applied at an effective rate of about from 6 to 21 million ITU/ft$^2$.

76. The method of claim 75 wherein the first dose is applied at an effective rate of about 8 million ITU/ft$^2$.

* * * * *